United States Patent
Chen et al.

(10) Patent No.: US 6,808,644 B2
(45) Date of Patent: Oct. 26, 2004

(54) CAPILLARY WITH GLASS INTERNAL SURFACE

(75) Inventors: Yu Chen, Singapore (SG); Janak Singh, Singapore (SG)

(73) Assignee: Institute of Microelectronics, Singapore (SG)

( * ) Notice: Subject to any disclaimer, the term of this patent is extended or adjusted under 35 U.S.C. 154(b) by 266 days.

(21) Appl. No.: 10/139,049

(22) Filed: May 2, 2002

(65) Prior Publication Data

US 2003/0205556 A1 Nov. 6, 2003

(51) Int. Cl.$^7$ .......................... B44C 1/22; C03C 15/00; C03C 25/68
(52) U.S. Cl. ...................................................... 216/33
(58) Field of Search ............................ 216/2, 31, 33, 216/36, 41, 17; 204/601; 156/99

(56) References Cited

U.S. PATENT DOCUMENTS

| | | | |
|---|---|---|---|
| 4,908,112 A | 3/1990 | Pace | 204/299 R |
| 5,376,252 A | 12/1994 | Ekstrom et al. | 204/299 R |
| 5,824,204 A | 10/1998 | Jerman | 204/601 |
| 5,869,004 A * | 2/1999 | Parce et al. | 422/100 |
| 6,176,962 B1 | 1/2001 | Soane et al. | 156/292 |
| 6,224,830 B1 | 5/2001 | Harrison et al. | 422/82.11 |
| 6,261,431 B1 | 7/2001 | Mathies et al. | 204/601 |
| 6,581,441 B1 * | 6/2003 | Paul | 73/61.52 |
| 2002/0110754 A1 * | 8/2002 | Skrobis | 430/313 |
| 2002/0134907 A1 * | 9/2002 | Bennett et al. | 249/135 |
| 2003/0178075 A1 * | 9/2003 | Moon et al. | 137/833 |
| 2003/0203271 A1 * | 10/2003 | Morse et al. | 429/38 |

OTHER PUBLICATIONS

D.J. Harrison et al., "Capillary Electrophoresis and Sample Injection Systems Integrated on a Planar Glass Chip," Anal. Chem. 64 (1992), pp. 1926–1932.

S.C. Jacobson et al., Effects of Injection Schemes and Column Geometry on the Performance of Microchip Electro–phoresis Devices, Anal. Chem. 66 (1994), pp. 1107–1113.

H.Y. Wang et al., "Low Temperature Bonding for Micro–Fabrication of Chemical Analysis Devices," Sensors and Acuators B 45 (1997), pp. 199–207.

* cited by examiner

Primary Examiner—Gregory Mills
Assistant Examiner—Roberts Culbert
(74) Attorney, Agent, or Firm—George O. Saile; Stephen B. Ackerman (57) ABSTRACT

A process to form a capillary that is well insulated from its environment is described. Said process has two stages. The first stage, which is the same for both of the invention's two embodiments, comprises forming a micro-channel in the surface of a sheet of glassy material. For the first embodiment, this sheet is bonded to a layer of oxide, that lies on the surface of a sheet of silicon, thereby sealing in the capillary. After all silicon has been selectively removed, a thin membrane of oxide remains. Using a low temperature bonding process, a second sheet of glassy material is then bonded to this membrane. In the second embodiment, the silicon is not fully removed. Instead, the oxide layer of the first embodiment is replaced by an oxide/nitride/oxide trilayer which provides improved electrical insulation between the capillary and the remaining silicon at a lower level of inter-layer stress.

16 Claims, 8 Drawing Sheets

CAPILLARY WITH GLASS INTERNAL SURFACE

FIELD OF THE INVENTION

The invention relates to the general field of microfluidics with particular reference to electrically isolatable microchannels.

BACKGROUND OF THE INVENTION

Micro-machined capillaries have found wide application in biological, pharmaceutical, and chemical applications. They also play an important role in micro-fluidic devices. They can be formed in various materials but, because of bio-compatibility considerations, surface hydrophilic properties, good electrical isolation, general chemical inertness, and good optical transparency, glass materials are often preferred, increasing the importance of being able to fabricate glass capillaries or capillaries having a glass internal surface.

The conventional approach to fabricating glass capillaries has been glass-to-glass fusion bonding. This requires special surface cleaning and treatment temperatures in the 500–700° C. range, which has a negative impact on process yield. To avoid the fusion bonding process, the anodic bonding process has been developed for glass to silicon dioxide bonding (typically on top of a silicon substrate). However, because silicon is opaque and the thickness of the oxide layer used for the bonding is low, straightforward application of anodic bonding limits the range of applications for its use. Another important limitation is that the thin oxide provides limited isolation from the electrically conductive silicon substrate so that only relatively low voltage differences between adjoining capillaries can be sustained.

Several methods to achieve a capillary with a glass internal surface have been described in the prior art. Fusion bonding of two glass plates, one of the plates having prefabricated channels on the internal surface, is one example of the prior art (D. J. Harrison, A. Manz, Z. Fan, H. Ludi, H. M. Widmer, Anal. Chem. 64(1992)1926–1932). A direct bonding technique was also developed in which the glass substrate and the cover plate were first surface hydrolyzed and then joined by hydrogen bonding, followed by annealing at 500° C. (S. C. Jacobson, R. Hergenroder, L. B. Koutny, R. J. Warmack, J. M. Ramsey, Anal. Chem. 66 (1994) 1107–1113). Anodic bonding of an oxidized silicon channel wafer to a glass plate has already been mentioned. Sodium silicate or potassium silicate bonding of glasses is a technique for forming a capillary with a glass internal surface using a low temperature process. However, as was the case for glass fusion bonding techniques, surface pre-cleaning and air bubble removal are very critical for achieving good bonding quality.

A routine search of the prior art was performed with the following references of interest being found:

In U.S. Pat. No. 4,908,112, Pace shows a wafer for analyzing biological samples using a capillary conduit. Glass to glass bonding by a polyamide gasket method has also developed by Pace and others. However, the internal surfaces for such types of capillary are of different materials, which may cause micro fluidic problems.

In U.S. Pat. No. 5,824,204, Jerman shows a micro-machined capillary device. Anodic bonding is used for bonding planar glass to a micro-fabricated silicon channel wafer with a partially oxidized, low stress nitride channel surface. After anodic bonding, the silicon is etched away, leaving glass and a partially oxidized nitride structure. This method has the advantages of good optical and electrical isolation properties because the silicon has been etched away. However, after the silicon has been removed, all that remains is a very thin partially oxidized low stress nitride film structure having three walls that form the channel. This makes for a fragile device structure, even if additional protection by polyamide is included.

Mathies et al. in U.S. Pat. No. 6,261,431 b1 show a process for a PCR-CE device. U.S. Pat. No. 6,224,830 b1 (Harrison et al.) shows an absorbance cell for micro-fluidic devices. U.S. Pat. No. 6,176,962 b1 (Soane et al.) shows an enclosed micro-channel structure method U.S. Pat. No. 5,376,252 (Ekstrom et al.) also shows a micro-fluidic structure.

The method to fabricate capillaries with glass internal surfaces that is disclosed in the present invention offers advantages such as good electrical isolation and optical properties as well as a lower process temperature relative to prior art processes.

SUMMARY OF THE INVENTION

It has been an object of at least one embodiment of the present invention to provide a process for manufacturing a capillary that is electrically insulated from its environment.

Another object of at least one embodiment of the present invention has been that said capillary be visible for optical inspection.

Still another object of at least one embodiment of the present invention has been that said capillary be mechanically robust.

A further object of at least one embodiment of the present invention has been to provide a process for manufacturing a capillary that possesses these qualities.

These objects have been achieved by means of a process having two stages. The first stage, which is the same for both of the invention's two embodiments, comprises forming a micro-channel in the surface of a sheet of glassy material. For the first embodiment, this sheet is bonded to a layer of oxide, that lies on the surface of a sheet of silicon, thereby sealing in the capillary. After all silicon has been selectively removed, a thin membrane of oxide remains. Using a low temperature bonding process, a second sheet of glassy material is then bonded to this membrane. In the second embodiment, the silicon is not fully removed. Instead, the oxide layer of the first embodiment is replaced by an oxide/nitride/oxide trilayer which provides good electrical insulation between the capillary and the remaining silicon.

BRIEF DESCRIPTION OF THE DRAWINGS

FIG. 21 is a plan view of the structure of the second embodiment of which FIG. 20 is a cross-section.

DESCRIPTION OF THE PREFERRED EMBODIMENTS

We will disclose the present through descriptions of two processes for manufacturing two embodiments of the invention. In the course of so doing the structure of the present invention will also become apparent.

1st Embodiment

Figure 1:
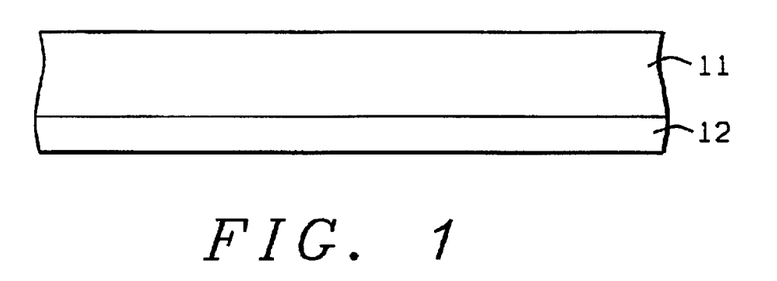
FIGS. 1–6 illustrate the process steps used to manufacture the first component of the structure of the present invention.
Figure 2:
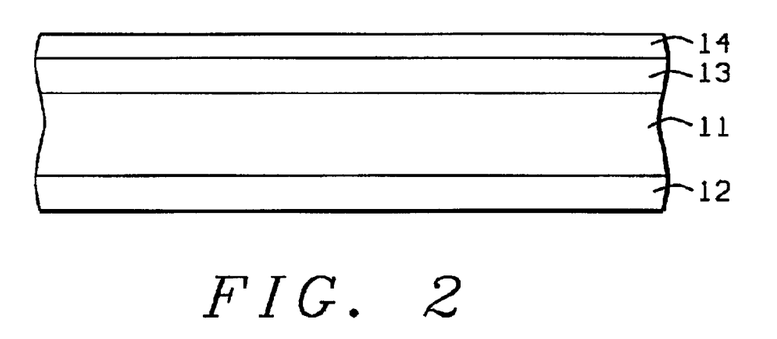

Referring now to FIG. 1, the process of the first embodiment begins with the provision of dielectric substrate 11 (typically glass) and depositing chromium layer 12 on its lower surface to a thickness between about 0.02 and 0.1 microns. As seen in FIG. 2, this is followed by the deposition on the upper surface of 11 of chromium layer 13 (to a thickness between about 0.02 and 0.1 microns) onto which is deposited gold layer 14 to a thickness between about 0.2 and 0.6 microns.

Figure 3:
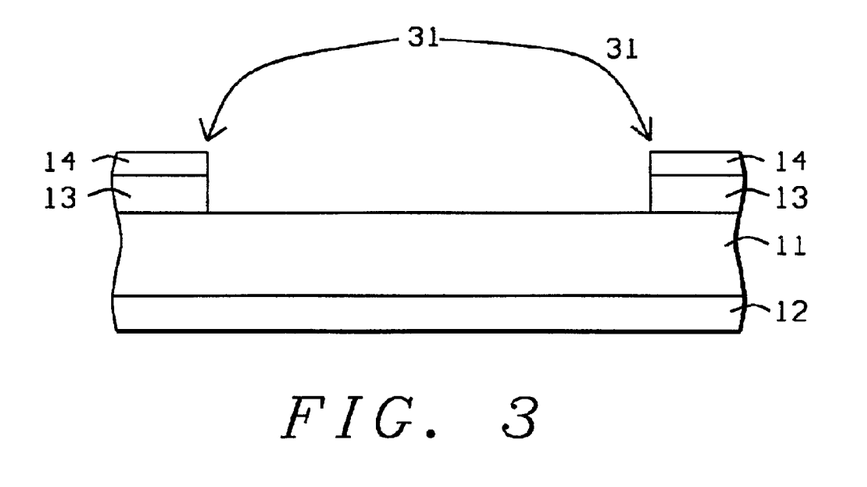
Figure 4:
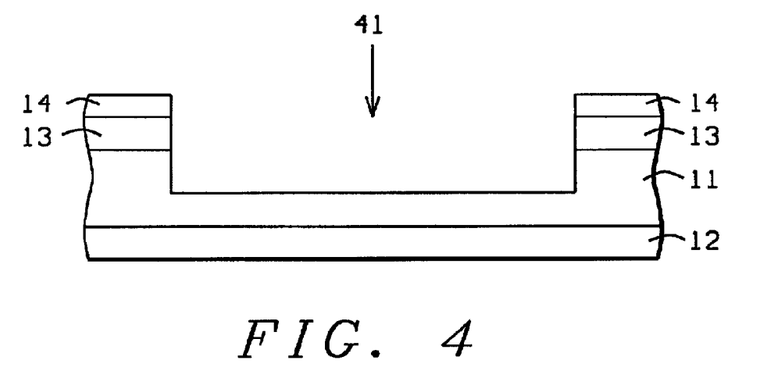
Figure 5:
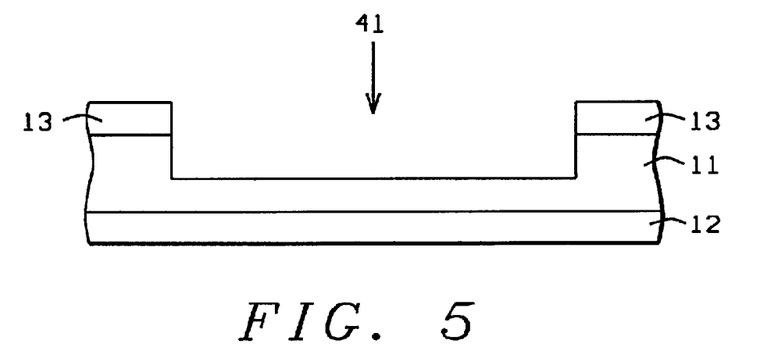
Figure 6:
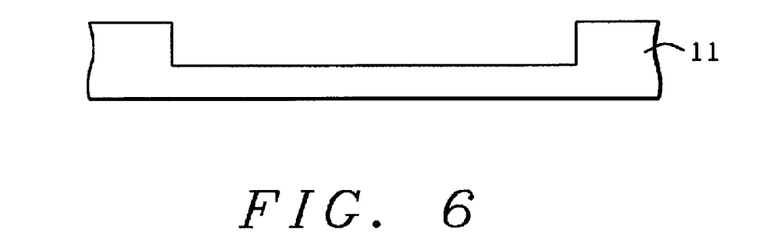

As shown in FIG. 3, gold-chrome layers 13/14 are patterned, using standard photolithographic methods to form a hard mask that defines the shape 31 of a micro-channel and then, using this hard mask, dielectric substrate 11 is etched to a suitable depth (typically between about 5 and 250 microns) thereby forming micro-channel 41 which is shown in cross-section in FIG. 4. Then, as seen in FIGS. 5 and 6, all gold and chromium are removed leaving the etched micro-channel in place thereby forming what we will refer to as the first component.

Figure 7:
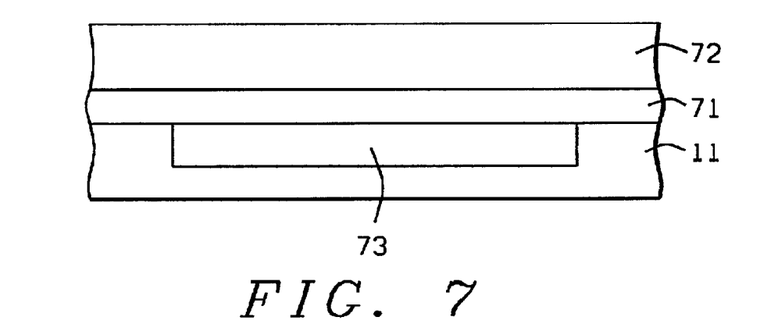
FIG. 7 shows the bonding of the first and second components that make up the first embodiment.

A second component is now formed from silicon sheet 72 (see FIG. 7) whose size is sufficient for it to be able to cover the first component. As shown in FIG. 7, a layer of silicon oxide 71 was formed on its lower surface, using plasma enhaced chemical vapor deposition (PECVD), following which layer 71 was bonded to the top surface of the first component, thereby forming capillary 73. Typically, anodic bonding was used to effect this step.

Figure 8:
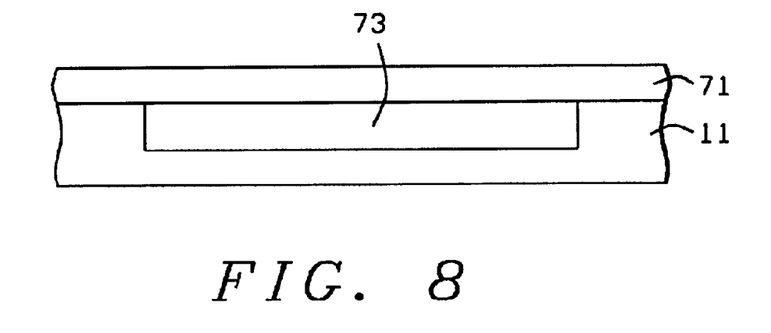
FIG. 8 shows formation of the capillary.
Figure 9:
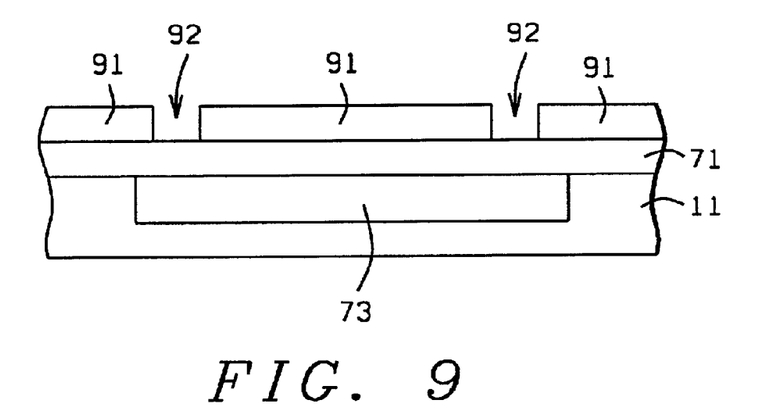
FIGS. 9 and 10 show alternate ways of forming access holes to the capillary.

Then, as shown in FIG. 8, all of silicon sheet 72 was selectively removed, leaving layer 71 unchanged and in place. This is followed by what is a key novel feature of the invention, namely the bonding of a sheet of transparent dielectric material 91 to layer 71 as illustrated in FIG. 9. The purpose of layer 91 is to provide mechanical strength to the structure. Since it is not required to provide a perfect seal for micro-channel 73 (this having been provided by layer 71), the bonding of layer 71 to layer 91 can be performed at a low temperature that is less than about 90° C. Among the processes that we have found suitable for use to accomplish this low temperature bonding we include sodium silicate bonding, potassium silicate bonding, and polydemethylsiloxane bonding. There are a number of possible materials and forms that are available for sheet 91. These include glass and polydemethylsiloxane sheets. The thickness of sheet 91 has typically been between about 0.25 and 1 mm.

Figure 10:
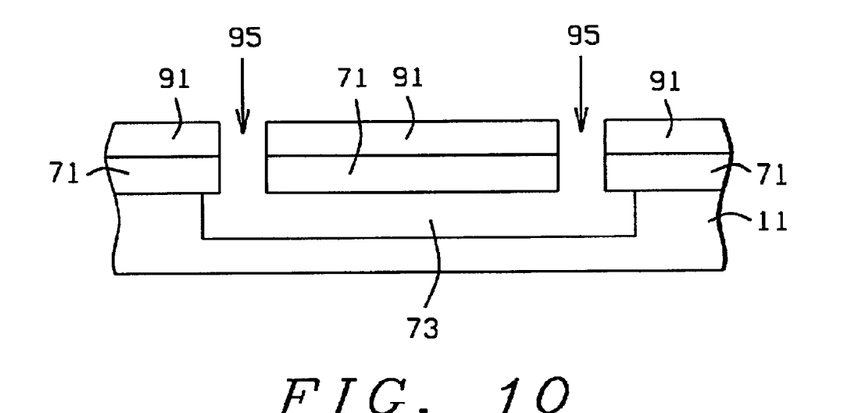

When sheet 91 is in position, it can be used as a hard mask 92 for the etching of access holes 95 from the outside world to the capillary as seen in FIGS. 9 and 10. An important feature of the present invention is that the formation of this hard mask can be accomplished either after sheet 91 has been bonded to layer 71 or suitable holes can be formed in sheet 91 (for example by being punched out) before it is bonded to 71.

2nd Embodiment

Figure 11:
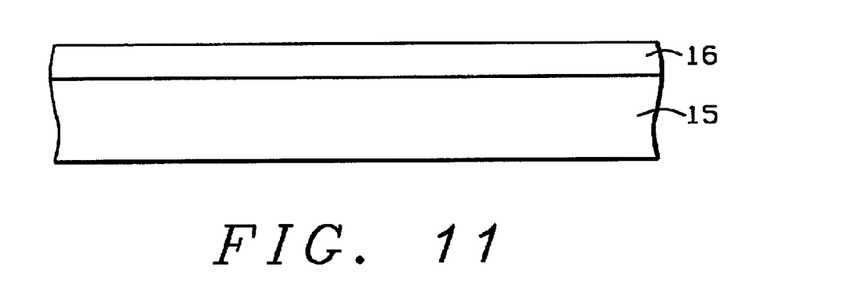
FIGS. 11–14 illustrate steps in the formation of the second component of the structure of the second embodiment.
Figure 12:
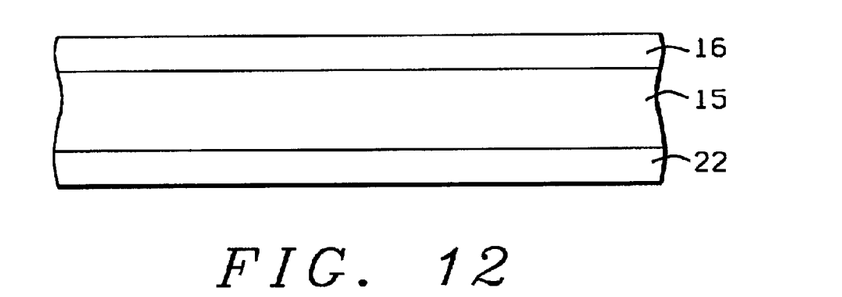

The second embodiment of the process of the invention also begins with the formation of first component 11 which can be revisited in FIG. 6. The process for the second component is, however, quite different. As shown in FIG. 11, it begins with silicon sheet 15 followed by the simultaneous growth of silicon oxide layers 16 and 22 (to a thickness between about 0.03 and 0.1 microns) on its upper and lower surfaces respectively (FIG. 12).

Figure 13:
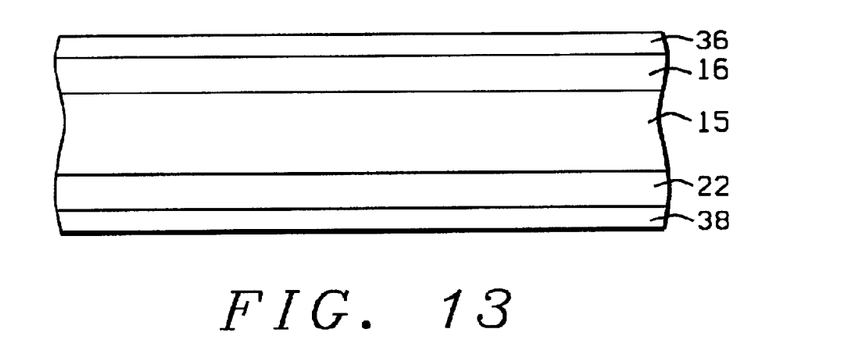
Figure 14:
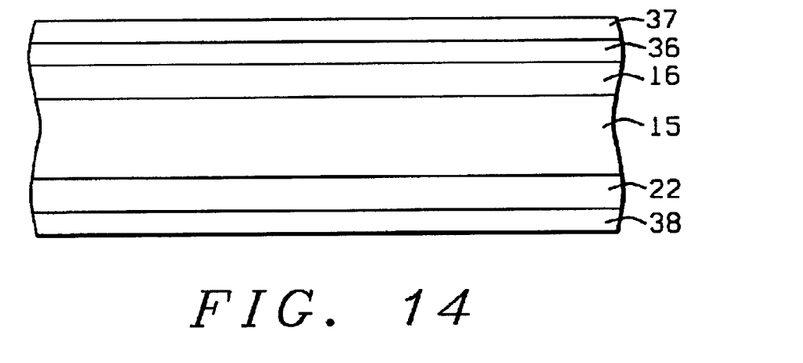
Figure 15:
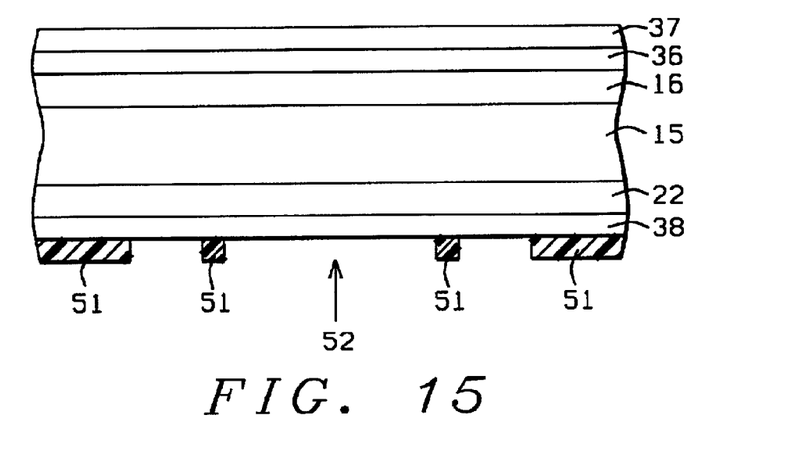
FIGS. 15 and 16 show the formation of a hard mask on the lower surface of the second component of the second embodiment.
Figure 16:
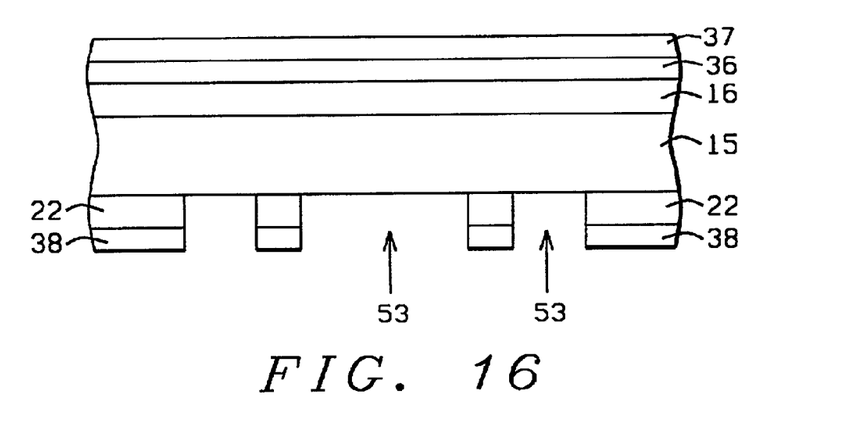

Next, silicon nitride layers 36 and 38 are simultaneously formed on silicon oxide layers 16 and 22 respectively (FIG. 13), to a thickness between about 0.1 and 0.2 microns, following which silicon oxide layer 37 is formed (to a thickness between about 0.2 and 0.5 microns) on silicon nitride layer 36 (FIG. 14). Then, photoresist mask 51 (FIG. 15) is used to form hard mask 53 from silicon nitride layer 38 (FIG. 16) which will be used during the formation of various openings needed by the structure.

Figure 17:
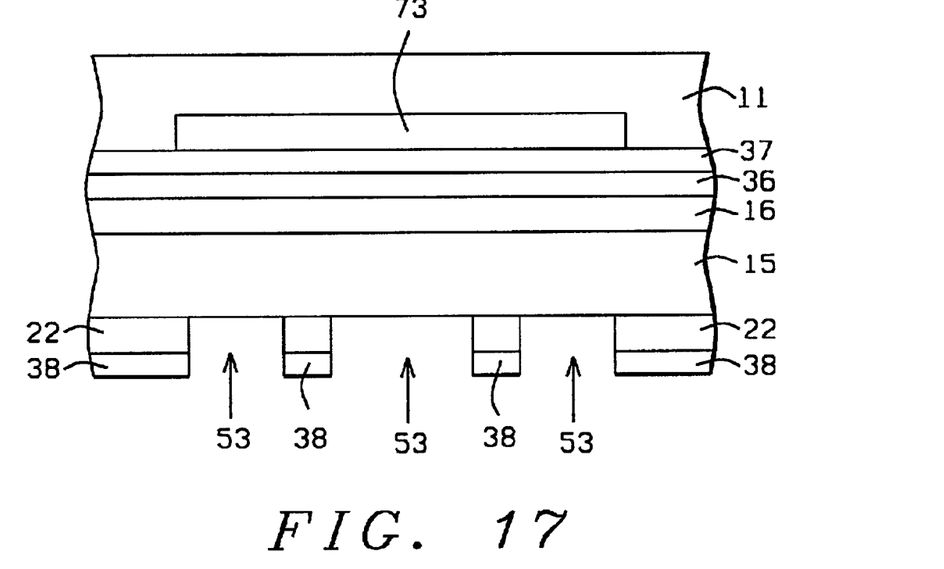
FIG. 17 shows the bonding of the first and second components that make up the second embodiment.
Figure 18:
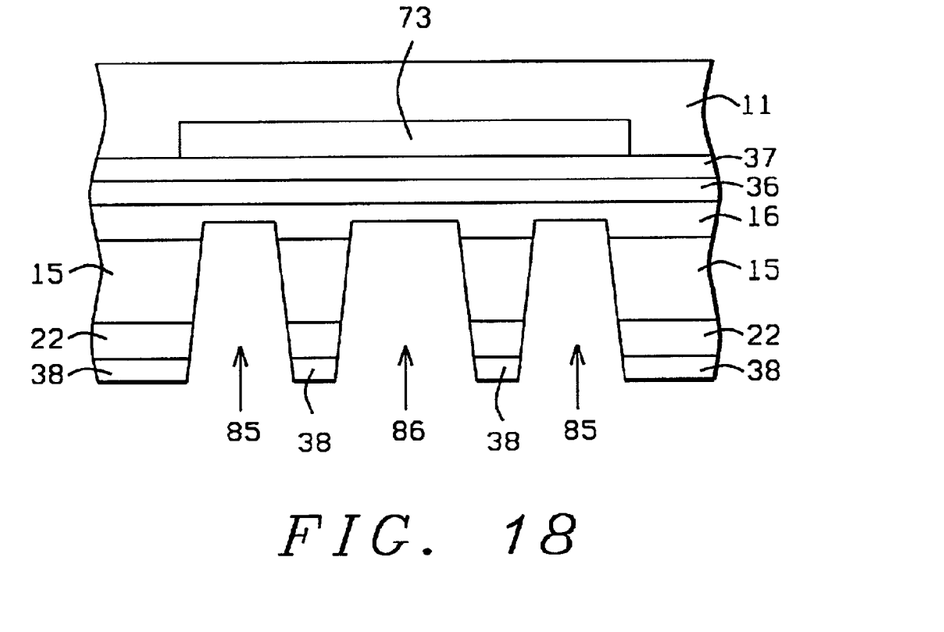
FIG. 18 shows the structure after openings have been formed using said hard mask.
Figure 19:
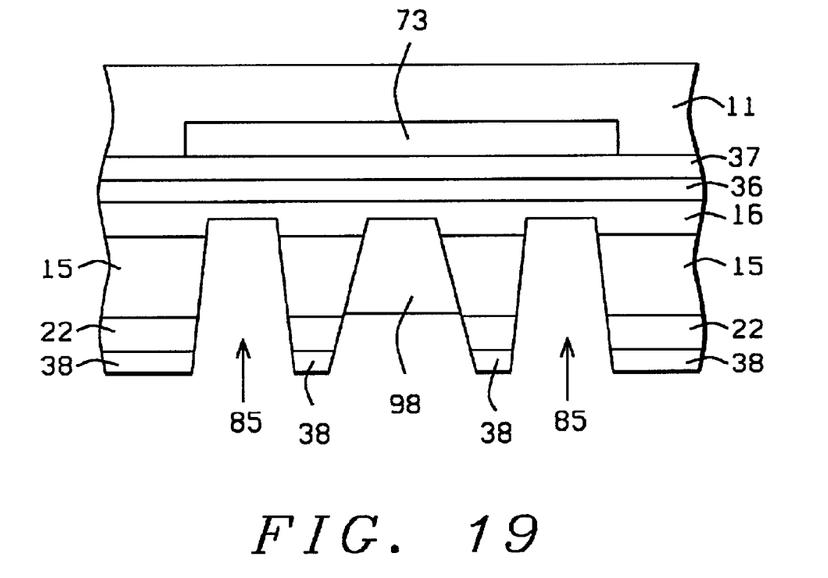
FIG. 19 shows the structure after selected openings have been filled with spin-on glass.
Figure 20:
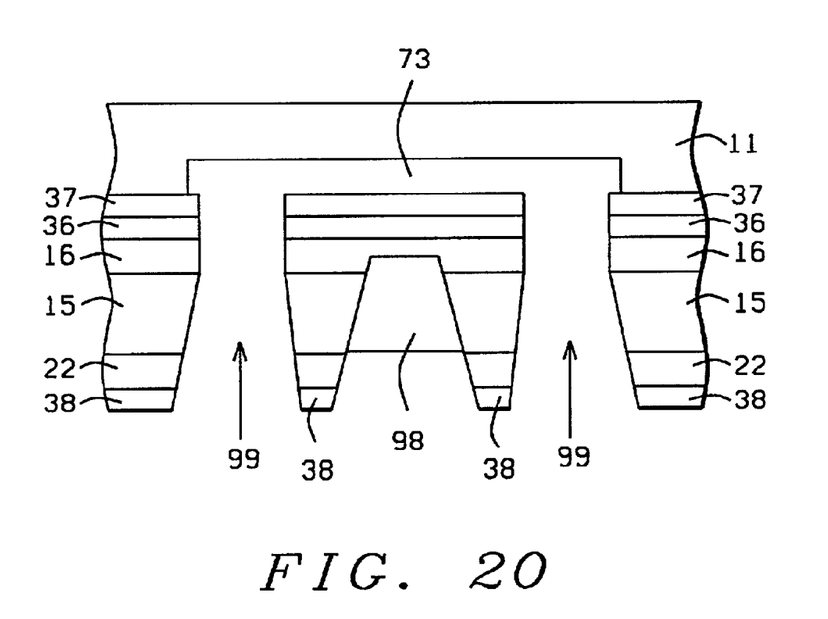
FIG. 20 shows how the unfilled openings have been etched through to the capillary.

These openings are then aligned relative to micro-channel 41 (see FIG. 5), following which the first component is bonded to silicon oxide layer 37, thereby forming capillary 73 as shown in FIG. 17. Then, then, using said silicon nitride hard mask, openings 85 and 86 are etched in silicon 15, as shown in FIG. 18, following which opening 86 is filled with spin on glass 98 as shown in FIG. 19. This allows etching of the unfilled openings to continue until thereby forming access holes 99 as shown in FIG. 20. Selective filling of openings such as 86 is achieved by dripping the solution directly into them and then spinning the wafer slowly so that it spreads out to form protective layer 98.

Figure 21:
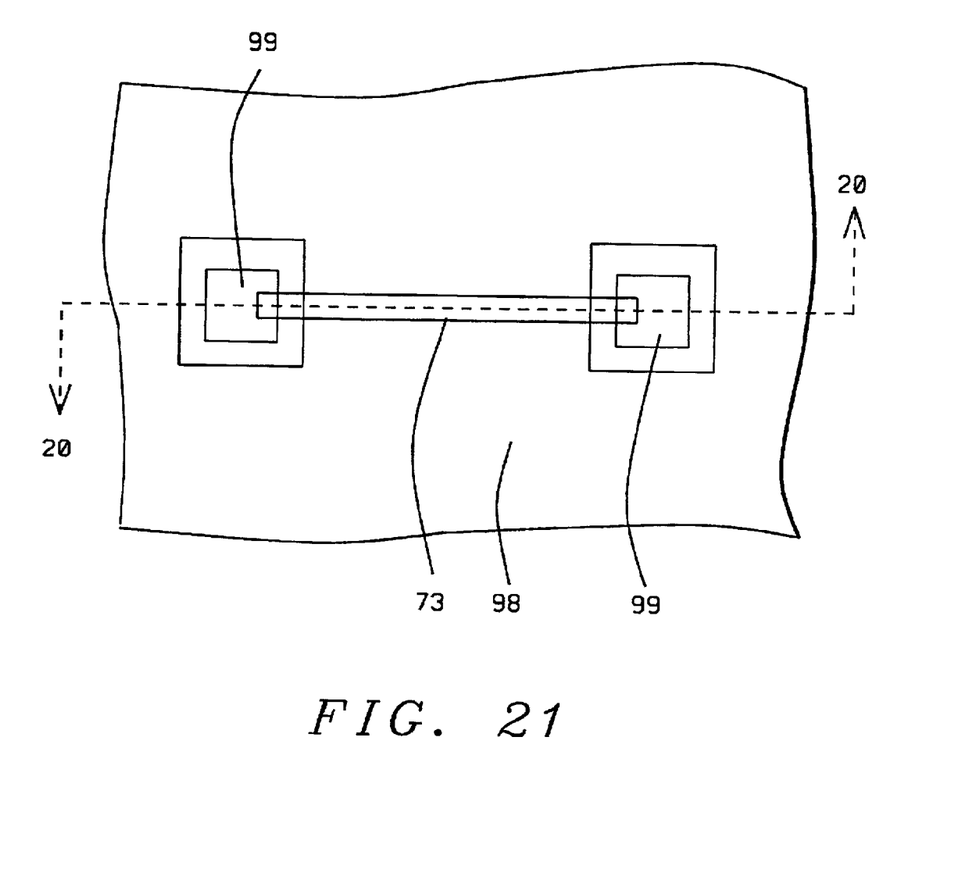

FIG. 21 is a plan view of the structure of the second embodiment, with FIG. 20 being a cross-section taken through 20—20 in FIG. 21.

The advantages of the second embodiment over the prior art are (a) the oxide/nitride/oxide trilayer combines superior insulation with lower internal stress relative to a single uniform layer of the same thickness and (b) the outer ring of silicon is available for locating storage reservoirs, inlet and outlet channels, etc.

What is claimed is:

1. A process to manufacture an electrically insulated capillary, comprising:

forming a micro-channel in an upper surface of a sheet of a first glassy material;

forming a layer of a second glassy material on a lower surface of a substrate;

bonding said first glassy material to said second glassy material, thereby forming said capillary;

selectively removing all material of which said substrate is formed; and then, at a temperature that is less than about 90° C., bonding a sheet of a transparent dielectric material to said second glassy material layer.

2. The process described in claim 1 wherein said sheet of transparent dielectric material is selected from the group consisting of glass and polydemethylsiloxane.

3. The process described in claim 1 wherein said sheet of transparent dielectric material has a thickness between about 0.25 and 1 mm.

4. The process described in claim 1 wherein the step of bonding said sheet of transparent dielectric material to said second glassy material layer is selected from the group of bonding processes consisting of sodium silicate, potassium silicate, and polydemethylsiloxane bonding.

5. The process described in claim 1 further comprising etching access holes to the capillary through said sheet of transparent dielectric material and said second glassy material layer after said sheet of dielectric material has been bonded to said second glassy material layer.

6. The process described in claim 1 further comprising etching access holes to the capillary through said sheet of transparent dielectric material prior to bonding to said second glassy material layer.

7. A process to manufacture a capillary, comprising:

providing a dielectric substrate having upper and lower surfaces;

depositing a layer of chromium on said lower surface and, on said upper surface, depositing a layer of chromium followed by a layer of gold;

patterning said gold-chrome layer to form a hard mask that defines said micro-channel and then, using said hard mask, etching said dielectric substrate to a depth, thereby forming a micro-channel;

then removing all gold and chromium form said upper and lower surfaces, thereby forming a first component;

providing a sheet of silicon having a lower surface and a size that is at least equal to that of said dielectric substrate;

on said lower silicon surface, forming a layer of silicon oxide;

bonding said layer of silicon oxide to said first component, thereby forming said capillary;

then selectively removing all silicon in said sheet while leaving said silicon oxide layer unchanged and in place; and then, at a temperature that is less than about 90° C., bonding a sheet of transparent dielectric material to said silicon oxide layer.

8. The process described in claim 7 wherein said sheet of transparent dielectric material is selected from the group consisting of glass and polydemethylsiloxane.

9. The process described in claim 7 wherein said sheet of transparent dielectric material has a thickness between about 0.25 and 1 mm.

10. The process described in claim 7 wherein the step of bonding said sheet of transparent dielectric material to said silicon oxide layer is selected from the group of bonding processes consisting of sodium silicate, potassium silicate, and polydemethylsiloxane bonding.

11. The process described in claim 7 further comprising etching access holes to the capillary through said sheet of transparent dielectric material and said silicon oxide layer after said sheet of dielectric material has been bonded to said silicon oxide layer.

12. The process described in claim 7 further comprising etching access holes to the capillary through said sheet of transparent dielectric material prior to bonding said sheet to said silicon oxide layer.

13. The process described in claim 7 wherein said layer of silicon oxide on said lower silicon surface is deposited by PECVD.

14. The process described in claim 7 wherein said layer of silicon oxide on said lower silicon surface is formed to a thickness between about 0.2 and 0.8 microns.

15. The process described in claim 7 wherein bonding said layer of silicon oxide to said first component, thereby forming said capillary is achieved using anodic bonding.

16. The process described in claim 7 wherein the depth to which said dielectric substrate is etched to form the micro-channel is between about 5 and 250 microns.

* * * * *